United States Patent [19]

Frank et al.

[11] Patent Number: 5,210,297

[45] Date of Patent: May 11, 1993

[54] WORKUP OF MOTHER LIQUORS RESULTING FROM THE PREPARATION OF ADIPIC ACID

[75] Inventors: Gerhard Frank, Hirschberg; Guenter Herrmann, Heidelberg; Gert Buerger, Mannheim; Jost H. Manegold, Lambsheim; Stefan Karbach, Neustadt; Ruediger Schmitz, Lambsheim, all of Fed. Rep. of Germany

[73] Assignee: BASF Aktiengesellschaft, Ludwigshafen, Fed. Rep. of Germany

[21] Appl. No.: 814,640

[22] Filed: Dec. 30, 1991

[30] Foreign Application Priority Data

Jan. 10, 1991 [DE] Fed. Rep. of Germany ....... 4100505

[51] Int. Cl.$^5$ .............................................. C07C 51/42
[52] U.S. Cl. .................................................... 562/593
[58] Field of Search ......................................... 562/593

[56] References Cited

U.S. PATENT DOCUMENTS 2,719,172  9/1955  Nebe ..................................... 423/24
3,106,450  10/1963  von den Berg ....................... 423/24

FOREIGN PATENT DOCUMENTS 920788  11/1954  Fed. Rep. of Germany ...... 562/593

Primary Examiner—José G. Dees
Assistant Examiner—Joseph M. Conrad, III
Attorney, Agent, or Firm—Herbert B. Keil

[57] ABSTRACT

A process for working up mother liquors resulting from the preparation of adipic acid by oxidation of cyclohexanol or cyclohexanone or mixtures thereof with nitric acid entails removal of nitric acid by azeotropic distillation with water, heating the resulting melt at from 130° to 180° C. and then dissolving it in water, treating the aqueous solution with cation exchangers, subsequently again evaporating off the water and heating the resulting dicarboxylic acid melt at from 200° to 240° C. and then obtaining a mixture of dicarboxylic acids by distillation.

3 Claims, No Drawings

WORKUP OF MOTHER LIQUORS RESULTING FROM THE PREPARATION OF ADIPIC ACID

The preparation of adipic acid by oxidation of cyclohexanol or mixtures of cyclohexanol and cyclohexanone in the presence of copper and vanadium catalysts with nitric acid results, after cooling and removal of the crystallized adipic acid, in a mother liquor which is recycled after replenishment with nitric acid. In order to avoid enrichment of byproducts, a portion of this mother liquor is drawn off and worked up. This results in a mixture of dicarboxylic acids, essentially adipic acid, glutaric acid and succinic acid. It is also an aim to recover the copper and vanadium catalysts for reuse for the oxidation.

German Patent 920,788 discloses the evaporation to dryness of mother liquors from adipic acid preparation after removal of the adipic acid under reduced pressure, the heating of the resulting residue at up to 200° C. until nitrogen oxide formation ceases, and the subsequent purification of the mixture of dicarboxylic acids by recrystallization or distillation. The mixture of dicarboxylic acids obtained in this way no longer meets the relevant requirements and, furthermore, the catalyst metals are lost.

In another process, which is described in U.S. Pat. No. 3,106,450, the mother liquor from adipic acid preparation is evaporated under reduced pressure at from 130° to 160° C., during which the nitric acid is removed by azeotropic distillation, and then sufficient water is added to produce a solution of pH 1.5-6. This solution is treated with an ion exchanger to remove the catalyst metal which can be recovered subsequently by elution from the ion exchanger. This process is also unsatisfactory with regard to the quality of the resulting dicarboxylic acids and, furthermore, the proportion of the catalyst metals recovered is in need of improvement.

It is an object of the present invention to obtain, from mother liquors resulting from adipic acid preparation, the mixture of dicarboxylic acids which has a minimum nitrogen content an is in yield and which can be reacted with polyols to give polyesterols with a low color number and, at the same time, a high proportion of the catalyst metals is recovered.

We have found that this object is achieved by a process for working up mother liquors resulting from the preparation of adipic acid by oxidation of cyclohexanol or cyclohexanone or mixtures thereof with nitric acid in the presence of copper and vanadium catalysts after removal of the adipic acid, which comprises the following steps a) removal of the nitric acid by azeotropic distillation with water under reduced pressure to result in a dicarboxylic acid melt containing copper and vanadium ions, b) heating said melt at from 130° to 180° C. to decompose nitrogen compounds and oxalic acid and result in a dicarboxylic acid melt containing copper and vanadium ions and having a reduced nitrogen content, c) dissolving said melt in water to form an aqueous solution containing dicarboxylic acids with a content of copper and vanadium ions, contacting said aqueous solution with a cation exchanger to bind the copper and vanadium ions and form an essentially copper- and vanadium-free dicarboxylic acid solution, e) removal of water by distillation from said solution to result in a melt of dicarboxylic acids, f) heating said melt at from 200° to 240° C. and g) obtaining a mixture of dicarboxylic acids by distillation.

The novel process has the advantage that the mixture of dicarboxylic acids is obtained in high yield, and the dicarboxylic acids have a lower nitrogen content and yield polyesterols with a low color number. The novel process has the further advantage that it is possible to recover a high proportion of the copper and vanadium catalysts.

The novel process starts from mother liquors obtained in the preparation of adipic acid by oxidation of cyclohexanol or cyclohexanone or mixtures thereof with nitric acid in the presence of copper and vanadium catalysts. Mother liquors of this type contain nitric acid, water, succinic acid, glutaric acid, adipic acid, copper, vanadium and iron ions, besides impurities. A typical mixture contains, for example, 30–36% by weight of nitric acid, 15–21% by weight of water, 10–13% by weight of succinic acid, 23–30% by weight of glutaric acid, 9–11% by weight of adipic acid, 0.7–0.8% by weight of copper, 0.08–0.09% by weight of vanadium, 0.002–0.004% by weight of iron plus other impurities such as nitrogen compounds.

In stage a), nitric acid is removed from the mother liquor by azeotropic distillation with water under reduced pressure to result in a dicarboxylic acid melt containing copper and vanadium ions. The pressure is advantageously from 50 to 200 mbar, in particular 100 to 150 mbar, and distillation is expediently continued up to 130° C. The dicarboxylic acid melt contains impurities plus adipic acid, glutaric acid, succinic acid and oxalic acid besides copper and vanadium ions.

In stage b), the dicarboxylic acid melt containing copper and vanadium ions is heated at from 130° to 180° C. to decompose nitrogen compounds and oxalic acid and result in a dicarboxylic acid melt containing copper and vanadium ions but with a lower nitrogen content. It is advantageous to heat at from 150° to 160° C. under a pressure of, for example, from 150 to 950 mbar. The melt is preferably kept at the stated temperature for from 5 to 45 min. The resulting mixture advantageously contains less than 1000 mg/kg nitrate ions, e.g. from 100 to 500 mg per kg of mixture of dicarboxylic acids.

In stage c), the melt which contains copper and vanadium ions and has a reduced nitrogen content is dissolved in water to form an aqueous solution containing dicarboxylic acids and copper and vanadium ions. The solution advantageously contains from 50 to 65% by weight of dicarboxylic acids and is expediently maintained at from 70° to 90° C. for from 30 to 60 min.

In stage d), the aqueous solution of dicarboxylic acids which contains copper and vanadium ions and has a reduced nitrogen content is contacted with a cation exchanger, and the copper and vanadium ions are bound, to result in an essentially copper- and vanadium-free dicarboxylic acid solution. The aqueous dicarboxylic acid solution is expediently passed over a bed of cation exchangers such as polystyrene containing sulfo groups. As soon as the exchanger layer is exhausted, copper and vanadium are recovered by elution with nitric acid. Surprisingly, after stage b) has been carried out, iron ions are not retained by the ion exchanger but are discharged with the dicarboxylic acid solution.

The dicarboxylic acid solution obtained in stage d), which is essentially copper- and vanadium-free and has a reduced nitrogen content, is distilled in stage e) to remove water, e.g. under a pressure of from 150 to 950 mbar up to from 130° to 180° C. and to result in a melt of dicarboxylic acids with a reduced nitrogen content.

In the next stage f), the dicarboxylic acid melt with reduced nitrogen content is heated at from 200° to 240° C., in particular from 210° to 230° C. The mixture of dicarboxylic acids is advantageously maintained at the stated temperature for from 1 to 4 h.

In subsequent stage g), dicarboxylic acid is obtained from the mixture of dicarboxylic acids by distillation. The distillation is advantageously carried out under reduced pressure, eg. from 5 to 20 mbar at from 180° to 200° C.

The resulting mixture of dicarboxylic acids has a very low nitrogen content and is suitable for preparing esters with polyols with a low color number.

The process according to the invention is illustrated in the following examples.

EXAMPLE 1

Copper and vanadium recovery by ion exchange after heavy metal nitrate decomposition and dicarboxylic acid distillation after previous decomposition of organic nitro compounds in the absence of copper and vanadium.

1 kg of molten mixture of dicarboxylic acids which has the following composition:

| | |
|---|---|
| dicarboxylic acids*) | 95.6% |
| free nitric acid | 0.2% |
| nitrate | 2.8% |
| copper | 1.2% |
| vanadium | 0.14% |
| iron | 0.005% |

*) including anhydrides, imides and nitro compounds (such as picric acid etc.)

and is obtained by removal of nitric acid by distillation from the mother liquor from the product of the oxidation of cyclohexanol with nitric acid and removal of the adipic acid, is maintained at 160° C. with stirring for 15 min, during which there is evolution of a gas composed of $NO_2$, $NO$, $N_2O$ and $N_2$ plus $CO$ and $CO_2$. The residue is 0.91 kg of a mixture of dicarboxylic acids with a nitrate content <0.05%, which is poured into water to prepare a 60% strength solution. The solution is maintained at 80° C. with stirring for 45 min and then passed over a suitable cation exchanger. The solution which is >99% freed of heavy metal ions is evaporated to dryness, and the resulting melt is heated at 230° C. for 2 h to decompose remaining oxalic acid and organic nitro compounds and is then distilled in a Sambay under 8 mbar with jacket temperatures of from 180° to 200° C. The distillation yield is 85% of a mixture of dicarboxylic acids (0.75 kg) with a nitrogen content of 0.06% and a polyetherol color number of 245 APHA.

After remaining dicarboxylic acids have been displaced from the ion exchanger and it has been washed with water, it is eluted with nitric acid. The eluate is employed in a test of the oxidation of cyclohexanol to adipic acid. The resulting adipic acid has a color number of 1.5 APHA.

COMPARATIVE EXAMPLE 1

1 kg of dicarboxylic acid melt of the composition described in Example 1 is maintained at 160°-170° C. under 950 mbar for 3 h until the initially violent evolution of gas ceases. The dark brown mixture of dicarboxylic acids is then passed in the form of a 60% strength aqueous solution over a suitable cation exchanger. The solution free of heavy metals is evaporated to dryness and then subjected to a Sambay distillation under the conditions described in Example 1 to yield 78% of a mixture of dicarboxylic acids with a nitrogen content of 0.27%; PEOL test: 1900 APHA.

The eluate obtained under comparable conditions produced an adipic acid with a color number of 14.6 APHA in the oxidation test. It should be noted that it is extremely difficult to wash the ion exchanger free of brown deposits.

COMPARATIVE EXAMPLE 2

1 kg of dicarboxylic acid melt of the composition described in Example 1 is maintained at 160°-170° C. under 950 mbar for 3 h until the initially violent evolution of gas ceases. A Sambay distillation is then carried out under the conditions stated in Example 1, the yield being only 52% because of the presence of copper and vanadium. Dicarboxylic acid data: nitrogen content 0.34%; PEOL test: 2600 APHA.

EXAMPLE 2

Removal of iron with and without previous decomposition of heavy metal nitrates 1 kg of dicarboxylic acid melt of the composition stated in Example 1 but containing 0.1% iron is subjected to thermal decomposition of heavy metal nitrates at 160° C. as described in Example 1 and is passed in the form of a 60% strength aqueous solution over the ion exchanger. Introduction of the dicarboxylic acid solution is stopped as soon as vandium/copper is detected in the discharge. Analysis by AAS shows that 70% of the iron was removed with the dicarboxylic acid solution.

Repetition of the experiment without decomposition of heavy metal nitrates resulted in all the ion being retained by the ion exchanger.

We claim:

1. A process for working up mother liquors resulting from the preparation of adipic acid by oxidation of cyclohexanol or cyclohexanone or mixtures thereof with nitric acid in the presence of copper and vanadium catalysts after removal of the adipic acid, which comprises the following steps
    a) removal of the nitric acid by azeotropic distillation with water under reduced pressure to result in a dicarboxylic acid melt containing copper and vanadium ions,
    b) heating said melt at from 130° to 180° C. to decompose nitrogen compounds and oxalic acid and result in a dicarboxylic acid melt containing copper and vanadium ions and having a reduced nitrogen content,
    c) dissolving said melt in water to form an aqueous solution containing dicarboxylic acids with a reduced nitrogen content and copper and vanadium ions,
    d) contacting said aqueous solution with a cation exchanger to bind the copper and vanadium ions and result in an essentially copper- and vanadium-free dicarboxylic acid solution,
    e) removal of water by distillation from said solution to result in a melt of dicarboxylic acids,
    f) heating said melt at from 200° to 240° C. and
    g) obtaining a mixture of dicarboxylic acids by distillation.

2. A process as claimed in claim 1, wherein the dicarboxylic acid melt is heated in stage b) for from 5 to 60 min.

3. A process as claimed in claim 1, wherein the dicarboxylic acid melt is heated in stage f) for from 1 to 3 hours.

* * * * *